United States Patent [19]
Kambin

[11] Patent Number: 5,762,629
[45] Date of Patent: Jun. 9, 1998

[54] OVAL CANNULA ASSEMBLY AND METHOD OF USE

[75] Inventor: Parviz Kambin, Devon, Pa.

[73] Assignee: Smith & Nephew, Inc., Memphis, Tenn.

[21] Appl. No.: 643,056

[22] Filed: May 2, 1996

Related U.S. Application Data

[63] Continuation-in-part of Ser. No. 198,551, Feb. 18, 1994, abandoned, which is a continuation-in-part of Ser. No. 784,693, Oct. 30, 1991, Pat. No. 5,395,317.

[51] Int. Cl.⁶ .................................................. A61M 5/178
[52] U.S. Cl. ............................ 604/164; 604/280; 604/282
[58] Field of Search ........................ 604/280, 281, 604/282, 164, 167, 131; 128/772

[56] References Cited

U.S. PATENT DOCUMENTS

| | | |
|---|---|---|
| 2,919,692 | 1/1960 | Ackermann . |
| 3,017,887 | 1/1962 | Heyer . |
| 3,508,554 | 4/1970 | Sheridan ................... 604/280 |
| 3,765,034 | 10/1973 | Johnston . |
| 3,941,127 | 3/1976 | Froning . |
| 4,368,738 | 1/1983 | Tersteegen et al. ............ 604/180 |
| 4,405,313 | 9/1983 | Sisley et al. .............. 604/280 X |
| 4,445,897 | 5/1984 | Ekbladh ..................... 604/280 |
| 4,539,976 | 9/1985 | Sharpe . |
| 4,545,374 | 10/1985 | Jacobson . |
| 4,573,448 | 3/1986 | Kambin . |
| 4,580,561 | 4/1986 | Williamson . |
| 4,638,799 | 1/1987 | Moore . |
| 4,678,459 | 7/1987 | Onik et al. . |
| 4,750,487 | 6/1988 | Zanetti . |
| 4,784,651 | 11/1988 | Hickey ................... 604/280 X |
| 4,919,130 | 4/1990 | Stoy et al. .................. 606/107 |
| 4,968,298 | 11/1990 | Michelson . |
| 5,004,457 | 4/1991 | Wyatt et al. . |
| 5,047,036 | 9/1991 | Koutrouvelis . |
| 5,059,170 | 10/1991 | Cameron ................ 604/280 X |
| 5,312,391 | 5/1994 | Wilk . |
| 5,601,576 | 2/1997 | Garrison .................... 606/148 |

OTHER PUBLICATIONS

Adam Schreiber et al., Does Percutaneous Nucleotomy With Discoscopy Replace Conventional Discectomy?, Jan. 1989, No. 238, pp. 35–42.

*Primary Examiner*—Sam Rimell
*Attorney, Agent, or Firm*—Pravel, Hewitt, Kimball & Krieger

[57] ABSTRACT

The present invention os a method and apparatus for performing percutaneous surgical disc procedures. The method includes percutaneously entering the back of a patient in a posterolateral position with an obturator and advancing the obturator through a percutaneously created fenestration of the annulus of the disc. A guide containing an oval shaped bore is placed over the obturator. An elongated member, having a cross-sectional shape such that when placed adjacent to the obturator forms an assembly having an oval cross-section, is inserted through the bore of guide and into the back of the patient and the fenestration of the annulus of the disc. The guide is removed and an oval cannula having a bore with an oval transverse cross-section and a proximal and distal end, is slid downwardly over the obturator and elongated member assembly. The distal end of the oval cannula is inserted into the disc. The obturator and the elongated member assembly are removed from the bore of the oval cannula and multiple surgical instruments are introduced into the oval cannula to perform the surgical procedure.

29 Claims, 12 Drawing Sheets

OVAL CANNULA ASSEMBLY AND METHOD OF USE

FIELD OF THE INVENTION

This application is a continuation-in-part application of U.S. Ser. No. 08/198,551, filed Feb. 18, 1994 abandoned which is a continuation-in-part application of U.S. Ser. No. 784,693 filed Oct. 30, 1991, now U.S. Pat. No. 5,395,317, issued Mar. 7, 1995.

This invention relates to surgery and specifically to a novel method and apparatus for accessing herniated intervertebral discs in a human patient.

BACKGROUND OF THE INVENTION

Low back pain syndrome with sciatica secondary to herniated intervertebral discs represents a major health problem in the United States. An intervertebral disc is a structure which occupies the space between the vertebrae and acts, among other things, as a shock absorbing cushion. A normal disc consists of two parts; a central part known as the "nucleus" and a surrounding part known as the "annulus" or "annulus fibrosis". The annulus degenerates with age, as does the nucleus. Degeneration of the disc is characterized by collagenation, in which some of the fluid content of the nucleus is lost and fragments of collagenized fibrous tissue are formed which float in the tissue fluid. At this stage of degeneration, external forces can readily increase the hydrostatic pressure on the nucleus, causing the fibers of the annulus to rupture. Nucleus fragments protrude. This, in turn, may cause pressure on the adjacent nerve root with resultant pain.

Degeneration of the disc may also be caused by other factors, for example, by accidental injury.

Several methods of treatment already exist. One method, usually referred to as "laminectomy" involves the surgical excision of the symptomatic portion of the herniated disc. This method of treatment has been used for many years, however, typical hospitalization time in nine days. Microsurgery has also been used in the treatment of herniated discs, in a procedure known as "microlumbar discectomy." This microsurgical procedure, although less invasive, nevertheless carries with it many of the complications associated with the older procedure, including injury to the nerve root and dural sac, perineural scar formation, reherniation of the site of the surgery, and instability due to excess bone removal. Another method of treatment is known as chemonucleolysis, which is carried out by injection of the enzyme chymopapain into the disc structure. This procedure has many complications including severe pain and spasm, which may last up to several weeks following injection. Sensitivity reactions and anaphylactic shock occur in limited but significant numbers of patients.

A further method of treatment, automated percutaneous lumbar discectomy, utilizes a specially designed needle which is inserted into a ruptured disc space. The nucleus of the disc is removed by suction instead of open surgery.

Another method of treatment is discussed in U.S. Pat. No. 4,573,448 and involves the percutaneous evacuation of fragments of the herniated disc through an access cannula positioned against the annulus of the herniated disc. A measure of safety and accuracy is added to this operative procedure by the artiroscopic visualization of the annulus and other important structures which lie in the path of the instruments, such as the spinal nerve.

While a considerable improvement over the existing procedures, nevertheless, this procedure does not enable the surgeon to directly view the resection of posterior nuclear fragments. That is, the internal diameter of the access cannula as described in U.S. Pat. No. 4,573,448 limits the design of an operating discoscope and limits the type and size of instruments that would allow for the visualization and simultaneous suction, irrigation and resection of the nuclear material.

The introduction of a second portal to the annulus from the opposite side of a first portal has been reported by Schreiber and his co-workers in *Clinical Orthopaedics and Related Research*, Number 238, page 36, January 1989. However, this bilateral, biportal procedure increases the operating room time, exposure to radiation by physician, patient and operating room personnel and also increases post-operative morbidity by involving both sides of the back and may cause excessive removal of nuclear material which increases the possibility for stenosis of the foramen and nerve root compression.

Thus, there is a need in the art for a percutaneous procedure to create an accessory unilateral portal in the annulus adjacent to an already positioned access cannula with a minimal additional exposure of the patient, physician and operating room staff to radiation and without unduly prolonging time spent in the operating room. A unilateral, biportal approach will allow for continuous visualization, identification and extraction of nuclear fragments from the disc under discoscopic control.

Large central herniations and partially extruded fragments may be visualized and evacuated. Such a unilateral approach to place more than one percutaneous portal in, for example, the L5-S1 vertebral joint, is also highly desirable because this procedure requires deflection of the patient's spine to enable access on the one side, causing a corresponding restriction of access on the opposite side. Moreover, by using a unilateral biportal approach, instruments do not need to traverse across the disc nucleus from a second portal remote from the symptomatic side. Therefore, the amount of non-symptomatic nuclear material removed by the unilateral approach is decreased as compared to the bilateral biportal approach. This is important in preventing collapse of disc approach. This is important in preventing collapse of disc space, which results in nerve compression and stenosis of the spinal canal. Also, another significant benefit of the unilateral approach is that the musculature and soft tissue and disc are traumatized on only one side of the back.

SUMMARY OF THE INVENTION

The present invention provides a percutaneous surgical disc procedure, comprising the steps of percutaneously entering the back of the patient in a posterolateral direction with an access cannula, advancing said access cannula through a first percutaneously created fenestration of the annulus of the disc, percutaneously entering the back of the patient in a posterolateral direction with an accessory cannula, and advancing said accessory cannula through a second percutaneously created fenestration of the annulus adjacent to and on the same side of the disc as the first fenestration.

The present invention also provides a method for the percutaneous decompression of a herniated intervertebral disc in a human patient, which comprises percutaneously entering the back of the patient in a posterolateral direction with an access cannula, advancing the access cannula into the disc through a first percutaneously created fenestration of the annulus of the disc, percutaneously entering the back of the patient in a posterolateral direction with an accessory cannula, advancing the accessory cannula into the disc through a second percutaneously created fenestration of the annulus adjacent to and on the same side of the disc as the first fenestration, removing nuclear material through one of the cannulae and observing the removal with an endoscope through the other.

The present invention also provides a guide means or jig for guiding the accessory cannula into the disc in an aligned relationship with the access cannula. In an alternate embodiment of the present invention a single oval cannula replaces the two cannulae through which both the procedure and the viewing can be performed.

In a broader sense, the present invention provides a method of percutaneously emplacing at least two cannulae in a patient, comprising percutaneously entering the back of the patient in a posterolateral direction with a first cannula and advancing the first cannula into the body of the patient to a position where the distal end of the first cannula is at a first predetermined location inside the body and the proximal end thereof projects beyond the outer surface of the back, securing a guide means to the proximal end of the first cannula and using the guide means to guide a second cannula as it percutaneously enters the back of the patient in a posterolateral direction and is advanced to a second predetermined location relative to said first predetermined location.

The method of the present invention requires only a small incision to place the cannulae, since this biportal approach utilizes unilateral placement. The unilateral biportal approach allows for continuous discoscopic control and visualization and provides adequate channels for fluid management, which significantly enhances the visual identification of the posterior annulus. The method in accordance with the invention may be carried out under local anesthesia, thus avoiding the risk of general anesthetics.

BRIEF DESCRIPTION OF THE DRAWINGS

A better understanding of the invention can be obtained when the detailed description of exemplary embodiments set forth below is reviewed in conjunction with the accompanying drawings, in which.

DETAILED DESCRIPTION OF A PREFERRED EMBODIMENT

In the description that follows, instruments are generally made out of suitable austenitic stainless steel, unless otherwise specified. While the surgical procedure described herein refers to decompression of intervertebral lumbar discs, it is to be understood that the procedure is not limited to lumbar discectomy and may be used in any procedure for percutaneously placing at least two cannulae in a patient, such as an intervertebral disc procedure or operation.

Figure 1:
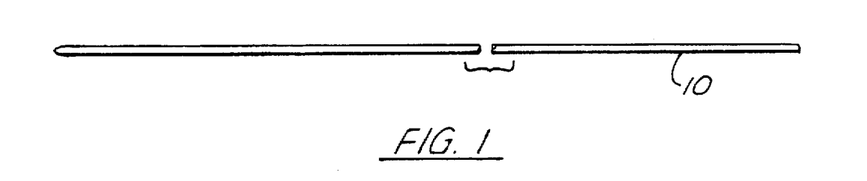
FIG. 1 is a plan view of a guide wire useful in the present invention.
Figure 2:
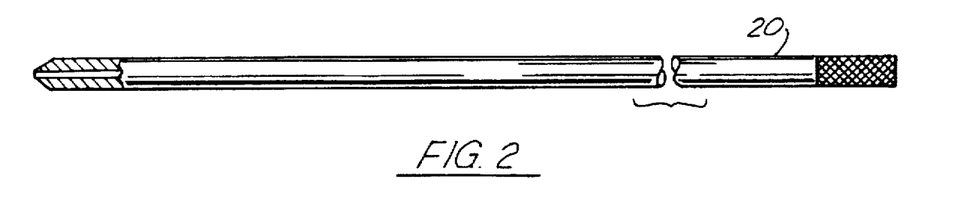
FIG. 2 is a plan view, partly in section, of a cannulated obturator useful in the present invention.
Figure 3:
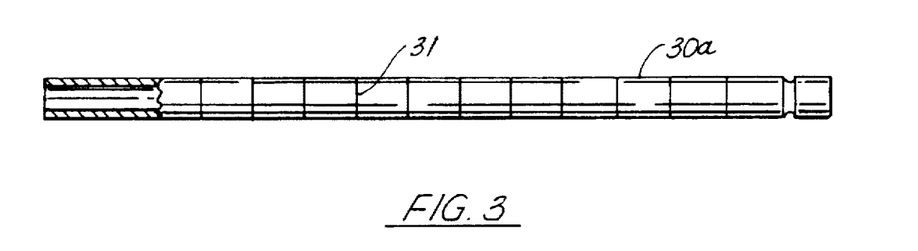
FIG. 3 is a plan view, partly in section, of an access cannula useful in the present invention.
Figure 4:
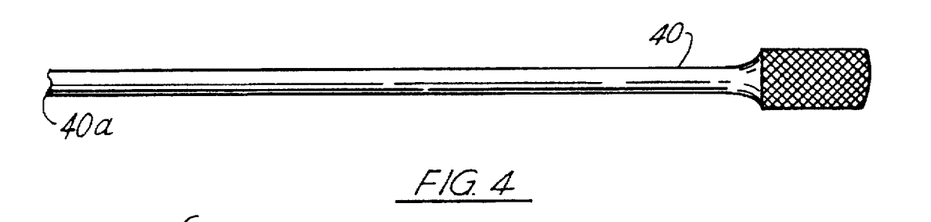
FIG. 4 is a plan view of a trephine useful in the present invention.

According to the method of the present invention, the patient is positioned on a radiolucent table in the appropriate prone or lateral position and a guidewire 10 (FIG. 1), suitably of about 0.050 in. diameter, is advanced through the skin of the back posterolaterally under fluoroscopic observation until the guidewire 10 contacts the exterior symptomatic side of the annulus fibrosis of the herniated disc. Thereafter, a cannulated obturator 20 (FIG. 2), having a lumen with a diameter slightly larger than that of the guidewire 10, is passed over the guidewire 10 until the cannulated obturator 20 contacts the external surface of the annulus fibrosis of the herniated disc. The removal of the guidewire 10 at this point is optional. An access cannula 30a (FIG. 3), suitably of about 0.25 in. outer diameter and having external gradations 31 of 10 mm, is then passed over the cannulated obturator 20 and advanced to the external surface of the annulus fibrosis. At this point, the guidewire 10 is removed if not previously removed. The inner diameter of the access cannula 30a is sized to closely fit over the cannulated obturator 20. The cannulated obturator 20 is then removed, and a 3 mm or 5 mm trephine 40 (FIG. 4) is introduced through the access cannula 30a. The trephine 40 has a plurality of saw teeth 40a or other cutting members. The trephine 40 is advanced into the annulus of the disc, with rotation, creating an annular fenestration (that is, a bore) through the annulus fibrosis into the nucleus. The trephine 40 is then removed.

The cannulated obturator 20 is reintroduced into the access cannula 30a and passed into the fenestration of the annulus. Fluoroscopic guidance may be utilized. The access cannula 30a is then advanced into the fenestration of the annulus, with rotary movement. After the access cannula is 30a is in the proper position, the cannulated obturator 20 is removed. The proximal end of cannula 30a projects beyond the surface of the patient's back (not shown) while the distal end is in the position shown in FIG. 10. The procedure described for placement of cannula 30a into the annulus of the disc follows the procedure described in U.S. Pat. No. 4,573,448. As is known, suitable local anesthetic is used as appropriate.

Figures 9, 10:
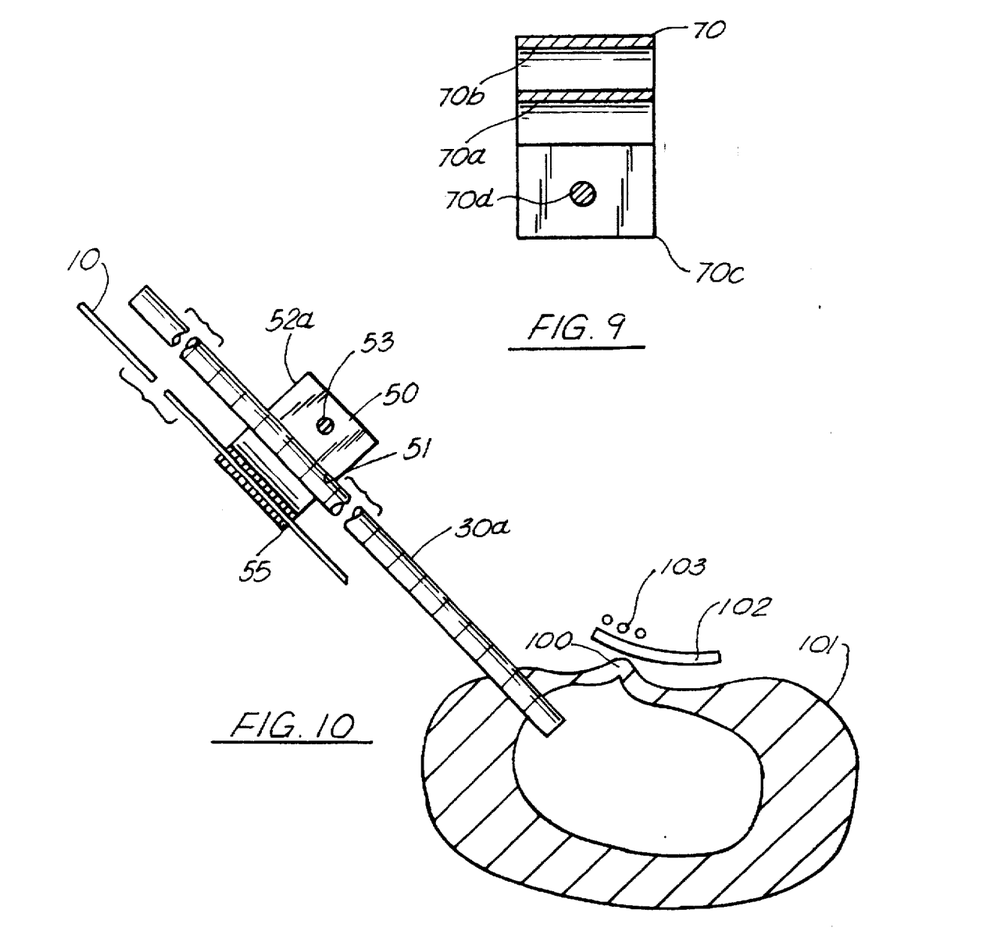
FIG. 9 is a view in section, taken along the lines 9—9 in FIG. 8.
FIG. 10 is a schematic view of a first access cannula inserted into the herniated disc.

Referring to FIG. 10, the procedure described above locates the distal end of the access cannula 30a adjacent the herniation 100 of the disc 101, which protrudes toward the posterior ligament 102 thus placing pressure on the nerves 103, which causes the pain characteristic of a herniated lumbar disc. First jig 50 (FIGS. 5, 6 and 10) is slid downwardly over the proximal end of the access cannula 30a by passing the access cannula 30a through the central bore 51 in the first jig 50. Jig 50 is secured in place near the proximal end of cannula 30a by tightening the screw 53 thereby clamping the legs 52a and 52b to the access cannula 30a.

Figure 5:
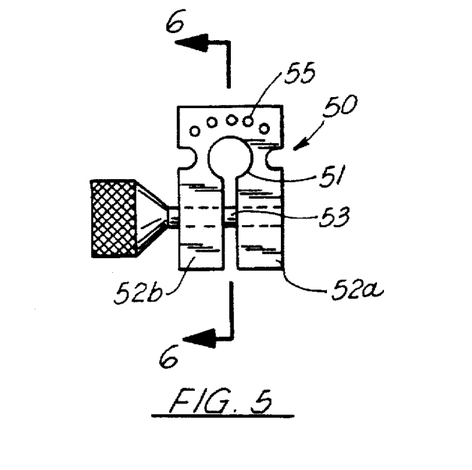
FIG. 5 is an elevational view of a first jig useful in the present invention.
Figure 6:
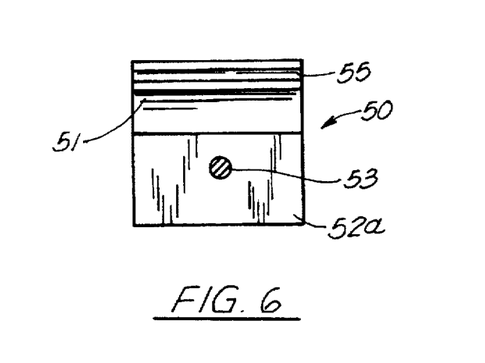
FIG. 6 is a view in section, taken along the lines 6—6 in FIG. 5.

First jig 50 preferably has a plurality of smaller bores 55 each having a diameter substantially the same as the diameter of the guidewire 10. The axes of the bores 55 are spaced from and are preferably parallel to the axis of the large bore 51. Alternatively, jig 50 may have only one smaller bore 55. Moreover, the bores 55 may be oblique to the axis of the large bore 51.

Under fluoroscopic observation, the guidewire 10 is slid through a selected one of the small bores 55 so that the guidewire 10 will ideally be centered on the annulus fibrosis. If necessary, a second guidewire 10 is passed through another of bores 55 and advanced toward the annulus fibrosis of the disc, while under fluoroscopic observation. Proper positioning of the guidewire on the annulus is determined by palpation and, if necessary, by fluoroscopy. The surgeon can then evaluate the placement of the guidewires and select the guidewire best positioned to provide the second fenestration of the annulus of the disc.

Having selected the desired guidewire 10, the other guidewire, if any, is removed, and the guidewire 10 is then introduced through the fibers of the annulus fibrosis for a distance of about three to about four millimeters. Jig 50 is removed, leaving the guidewire 10 and access cannula 30a in place.

Figure 8:
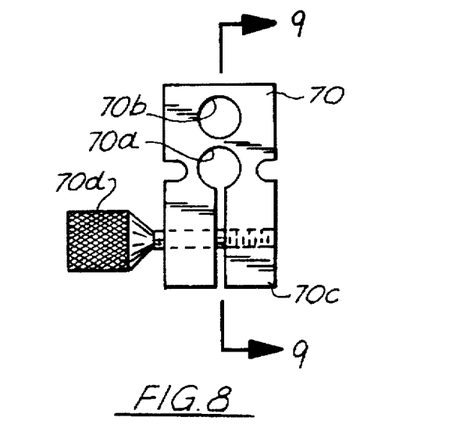
FIG. 8 is an elevational view of a second jig useful in the present invention.
Figure 11:
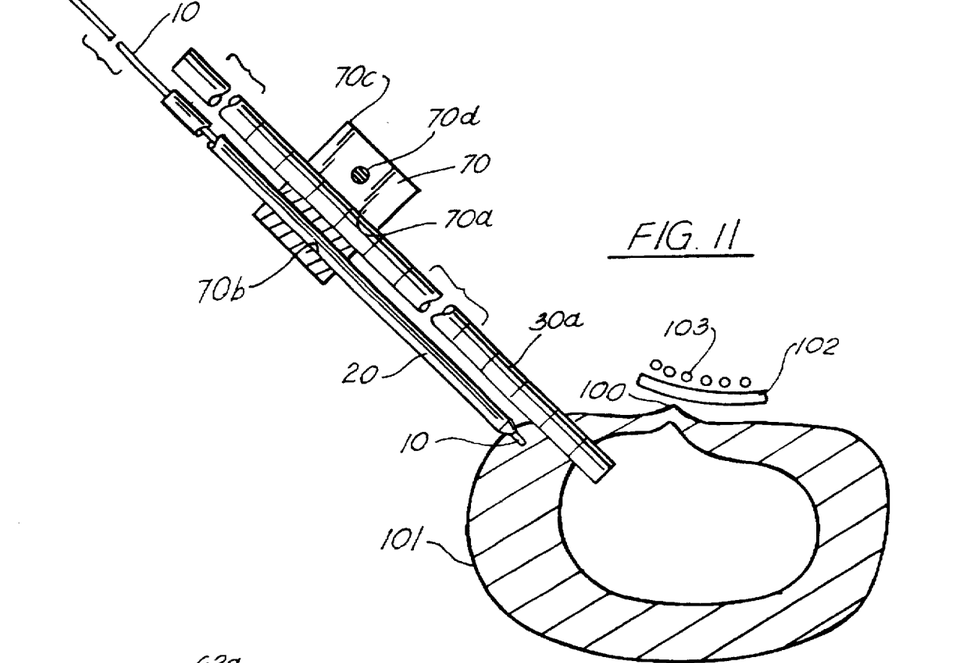
FIG. 11 is a view similar to FIG. 10 showing the use of the second jig to index a second accessory cannulae relative to the first access cannula.

Second jig 70 (FIGS. 8, 9 and 11) is secured to access cannula 30a near the proximal end by passing access cannula 30a through bore 70a, passing the guidewire 10 through bore 70b, and clamping legs 70c together by means of screw 70d. Cannulated obturator 20 is then advanced over the guidewire 10 by rotary movement through the bore 70b of the second jig 70 until the cannulated obturator 20 contacts the annulus fibrosis, as shown in FIG. 11. The guidewire 10 and jig 70 are removed leaving the cannulated obturator 20 in place. An accessory cannula 30b is passed over the cannulated obturator 20 and advanced toward the annulus fibrosis. Accessory cannula 30b is sized to slide in the annulus between bore 70b and the outer surface of cannulated obturator 20. The cannulated obturator 20 is then removed, leaving the accessory cannula 30b in place. While it is presently preferred that cannulae 30a, 30b have the same inner and outer diameters, one may have a smaller inner and/or outer diameter than the other. Although it is presently preferred to use the second jig 70, it is not necessary to do so.

Figure 13:
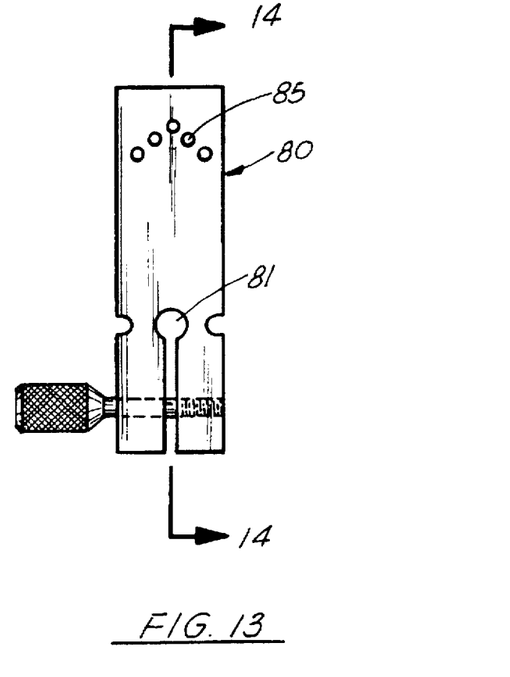
FIG. 13 is an elevational view of an alternate embodiment of a first jig of the present invention.
Figure 14:
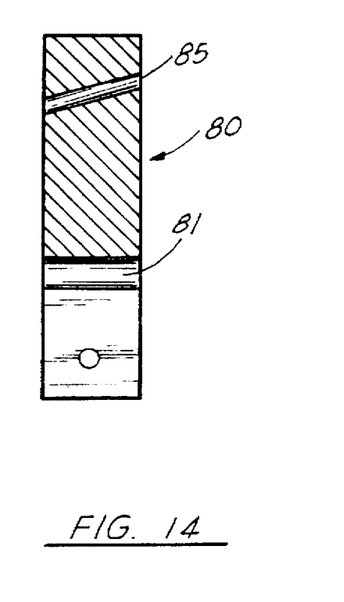
FIG. 14 is a view in section, taken along the lines 14—14 in FIG. 13.
Figure 17:
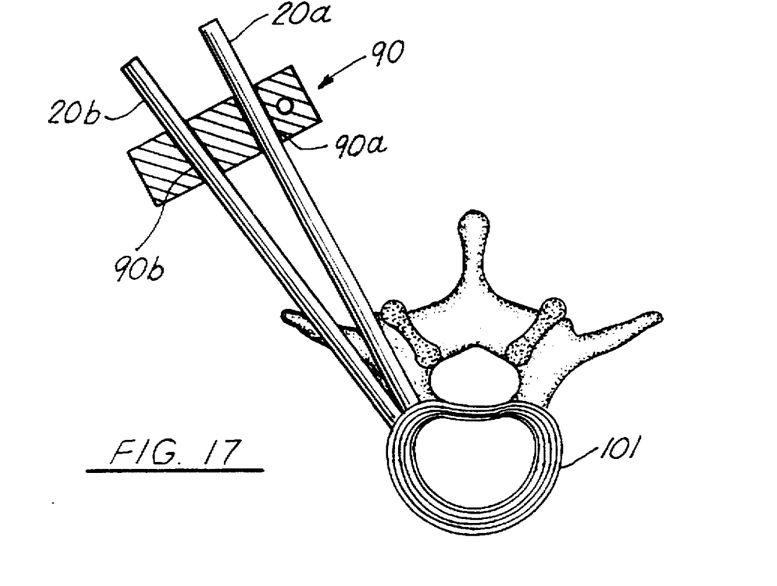
FIG. 17 is a schematic view of an access cannula and a converging accessory cannula inserted into the disc.

In certain circumstances it may be desirable to insert the accessory cannula 30b at an angle relative to the access cannula 30a so that the cannulae 30a and 30b converge at or near their tips (FIG. 17). In this situation a jig is used which has one or more of the bores positioned oblique to the center bore rather than parallel to it. A jig 80 (FIGS. 13 and 14) is provided which is identical in structure to jig 50 except for the axis of the smaller bores 55. In jig 80 a plurality of smaller bores 85 have an axis that is at an angle relative to the longitudinal axis of a large bore 81. The angle of the axis of the smaller bores 85 can be between about 10° to 50° and is preferably 30° relative to the longitudinal axis of the large bore 81 as shown in FIG. 14. The converging cannulas can be most useful in extra discal surgery and for foraminal surgery or surgery inside of the spinal canal for direct visualization and retrieval of sequestrated fragments.

Figure 15:
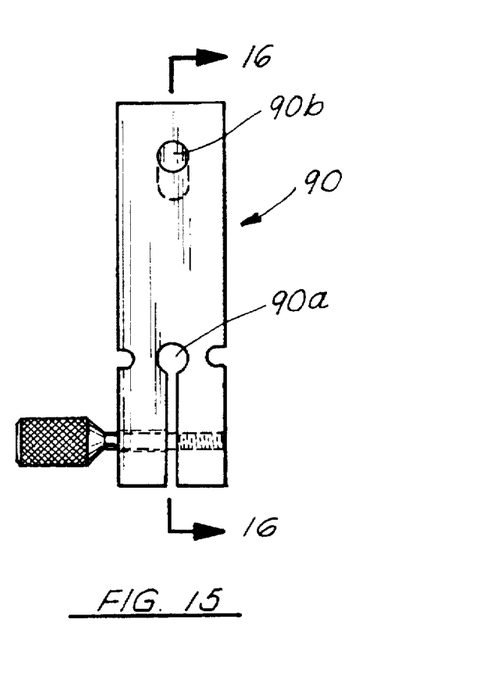
FIG. 15 is an elevation view of an alternate embodiment of a second jig of the present invention.
Figure 16:
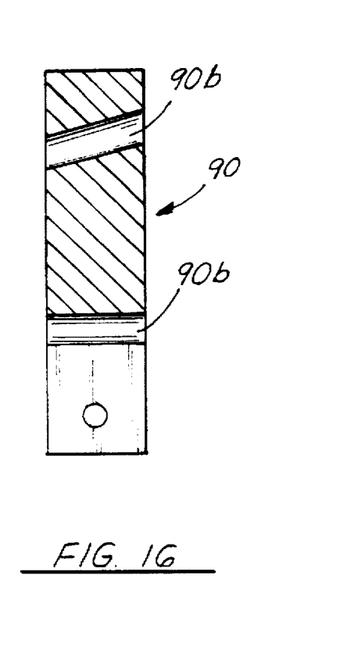
FIG. 16 is a view in section, taken along the line 16—16.

A jig 90 (FIGS. 15 and 16) is also provided which is identical in structure to jig 70 except for the axis of the bore 70b. In jig 90 a bore 90b has an axis that is at an angle relative to the longitudinal axis of a central bore 90a. The angle of the axis of the bore 90b can be between about 10° to 50° and is preferably 30° relative to the longitudinal axis of the central bore 91 as shown in FIG. 16. Both of the jigs 80 and 90 are used in the method of the present invention in the same manner as jigs 50 and 70 are used.

The annulus fibrosis is inspected endoscopically through the accessory cannula 30b, and if satisfactory, a trephine 40 is passed through the accessory cannula 30b and a second fenestration is cut through the annulus fibrosis into the nucleus. The trephine 40 is then removed. The accessory cannula 30b is advanced into the annulus. Introduction of both cannulae into the annulus of the disc under fluoroscopic observation is carried out in a manner known per se, such as described in U.S. Pat. No. 4,573,448.

Fragments of the herniated disc can be removed through the desired cannula 30a and 30b by inserting a trephine 40 in the desired cannula and moving it back and forth within the nucleus of the herniated disc as suction is applied. Alternatively, the trephine can be removed and suction may be applied through the cannula itself. In another method, forceps, trimmer blades, suction punch forceps laser lights, etc. are used to remove such fragments via one of the cannula.

Figure 7:
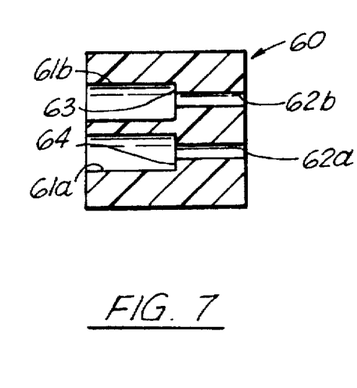
FIG. 7 is an elevational view in section of a sealing adaptor useful in the present invention.
Figure 12:
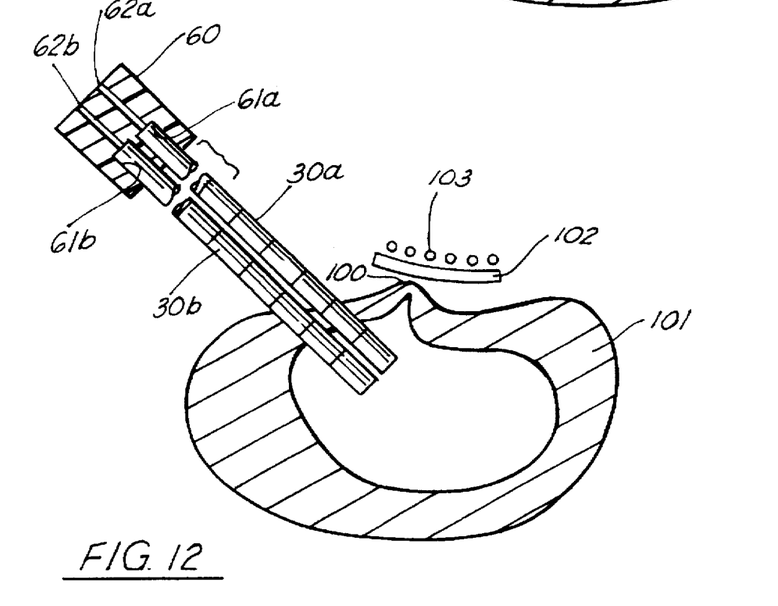
FIG. 12 is a schematic view showing two cannulae placed in the body of the patient with the sealing adaptor of FIG. 7.

Preferably, however, before removal of nuclear material, a sealing adaptor 60 (FIG. 7), which is suitably comprised of silicon rubber, is attached to the proximal extremity of the access cannula 30a and accessory cannula 30b, as shown in FIG. 12 with access cannula 30a and accessory cannula 30b received in bores 61a and 61b of sealing adaptor 60. Insertion of access cannula 30a and accessory cannula 30b into the sealing adaptor will stop when the cannulae contact shoulders 63 and 64, respectively of bores 61a and 61b. Nuclear evacuation through one of the cannulae 30a or 30b and simultaneous arthroscopic observation via the other of cannulae 30a or 30b is possible by sealingly passing an arthroscope (not shown) into one of bores 62a and 62b and thence into one of cannula 30a or 30b, while a tool (not shown) is inserted into the other bore and thence into the other cannula. Nuclear material may then be evacuated by a conventional powered surgical instrument (not shown) through the access cannula 30a or accessory cannula 30b while under arthroscopic observation through the other cannula. A saline solution may be passed via the arthroscope through one cannula and excess fluid may be evacuated through the other cannula. Direct visualization of the resection of the desired disc material is thus made possible.

In an alternate embodiment of the present invention the surgical procedure and viewing can be done through a single oval cannula 110 rather than the cannulae 30a and 30b. The oval cannula 110 provides a broader access to the intervertebral disc and is particularly useful for arthroscopic decortation of the vertebral plates in preparation for percutaneous interbody fusion. Further, when performing posterior or posterolateral fragmentectomy via an intradiscal access, the oval cannula 110 allows for further angulation of the inserted instruments and provides a better access to the posterior herniations.

Figures 18, 22:
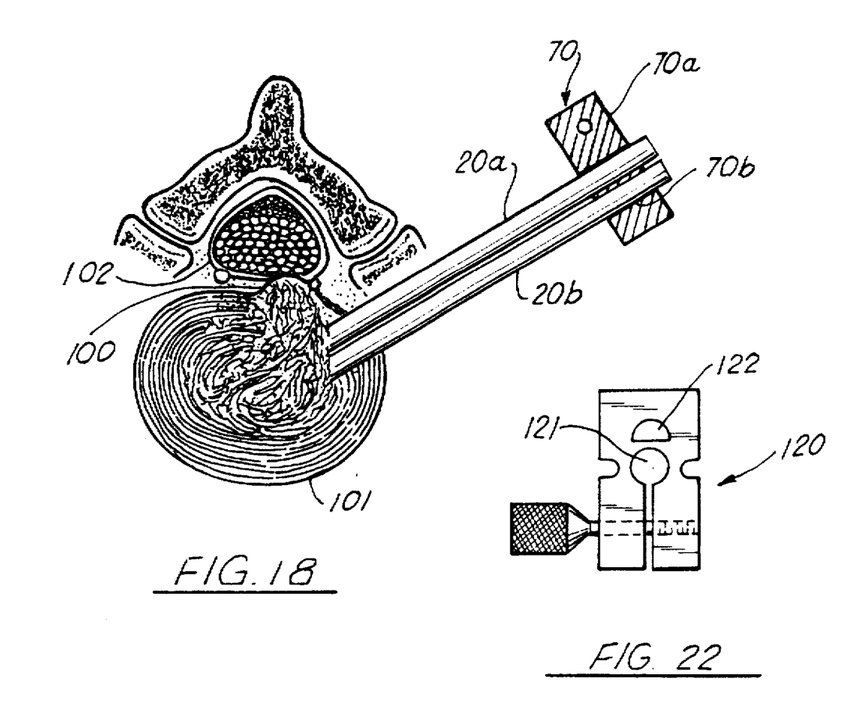
FIG. 18 is a schematic view of two cannulae inserted into the herniated disc.
FIG. 22 is an elevational view of a second alternate embodiment of a jig of the present invention.
Figures 19, 20:
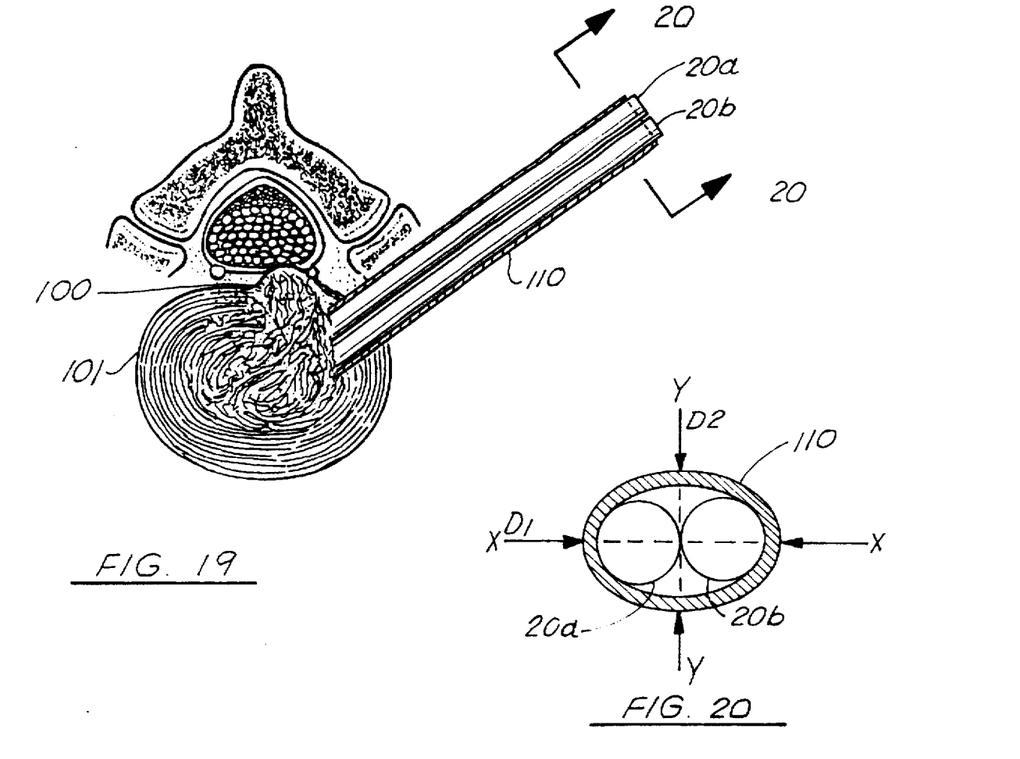
FIG. 19 is a schematic view of an oval cannula inserted over the two cannulae shown in FIG. 18.
FIG. 20 is a view in section, taken along the lines of 20-20 in FIG. 19.
Figure 21:
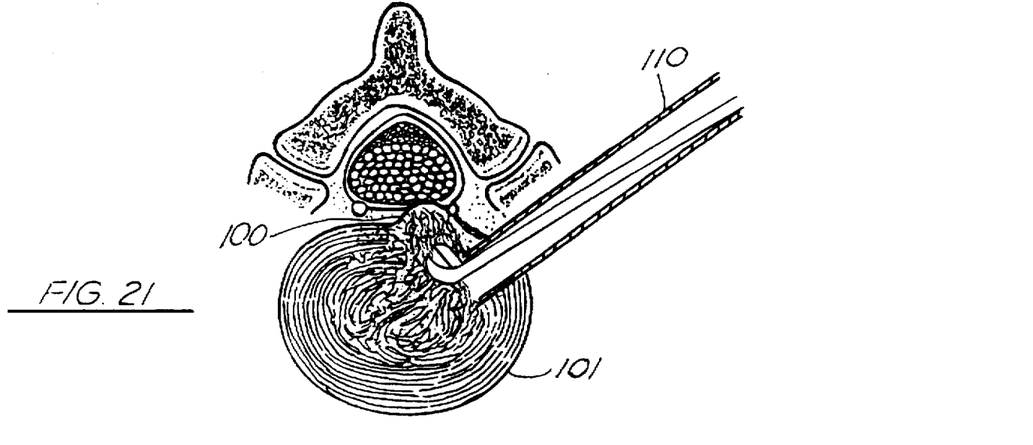
FIG. 21 is a schematic view of a procedure being performed through an oval cannula inserted into the herniated disc.

If this alternate method is used two cannulated obturators 20 or cannulas 30a, 30b are inserted into the disc 101 in the manner described above using the jig 70 to align the obturators 20 or cannulae 30a, 30b in parallel alignment as shown in FIG. 18. The jig 70 is removed and the oval cannula 110, slightly larger in diameter than the two obturators 20a, 20b or cannulae 30a, 30b, is slid downwardly over the obturators 20a, 20b or cannulae 30a, 30b and inserted into the annulus fibrosis (FIGS. 19 and 20). The obturators 20a, 20b or cannulae 30a, 30b are removed and the surgical procedure and viewing are performed through the single oval cannulae 110 (FIG. 21). The oval cannula 110 has a uniform inner and outer diameter and a transverse cross section that is defined by an X axis D1 and a Y axis D2 (FIG. 20). The Y axis D2 has a dimension generally between about 3 to 11 millimeters and the X axis D1 has a dimension of generally between about 5 to 22 millimeters and a longitudinal length of generally between about 50 to 250 millimeters. These dimensions will accommodate the variety of obturators 20 and cannulae 30 used in the method of the invention.

If the surgical procedure is performed on a patient having a small disc space, a half circle cannula of a type known in the industry can be used with an alternate jig 120 having a central bore 121 and a second bore 122 in the shape of a half circle as shown in FIG. 22. An oval cannula 110 with a smaller diameter can then be slid over the cannulae to provide a working channel which will fit into the smaller disc space.

Figures 25, 25A, 26:
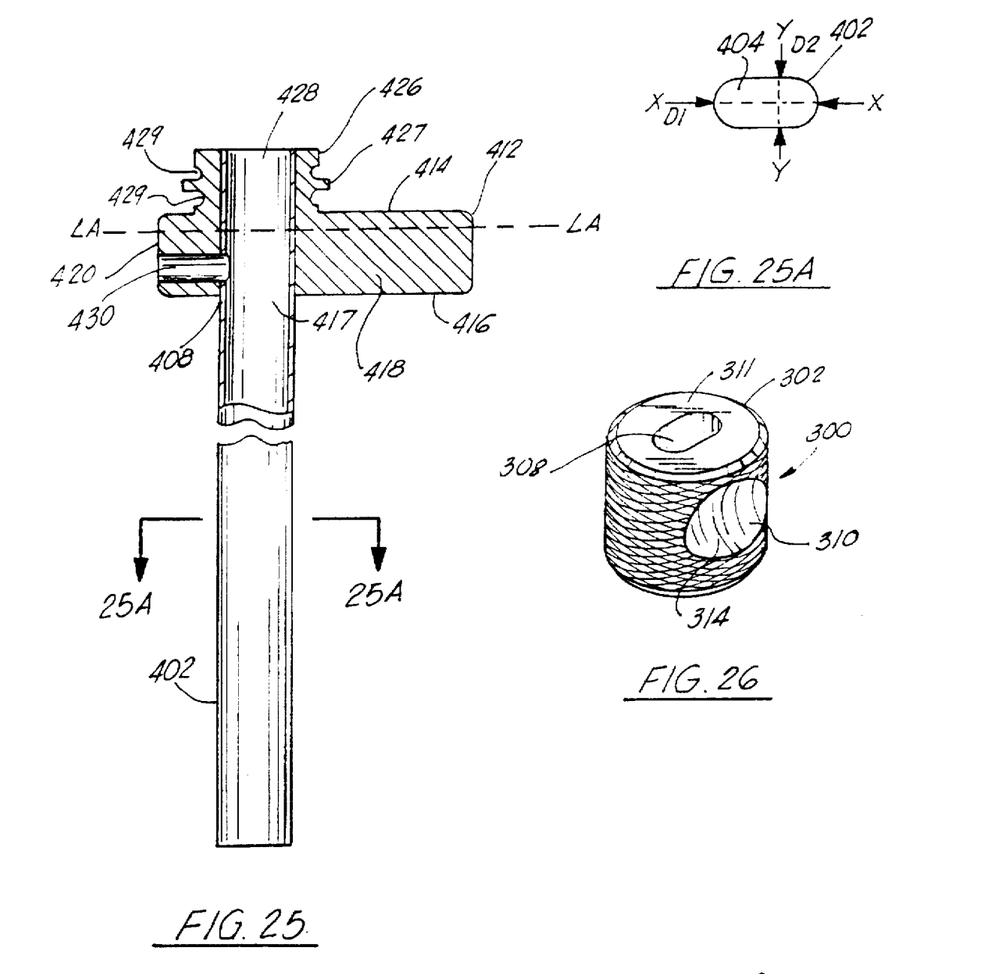
FIG. 25 is a side plan view in partial cross section of the oval cannula apparatus of FIG. 23.
FIG. 25A is a cross-sectional view of the oval bore of the oval cannula apparatus of FIG. 23 along the lines of 25A—25A of FIG. 25.
FIG. 26 is a perspective view of an alternate embodiment of the subject invention illustrating a guide member.
Figure 27:
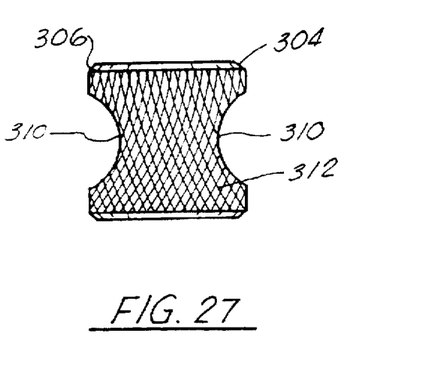
FIG. 27 is a side plan view of the guide member of FIG. 26.
Figure 28:
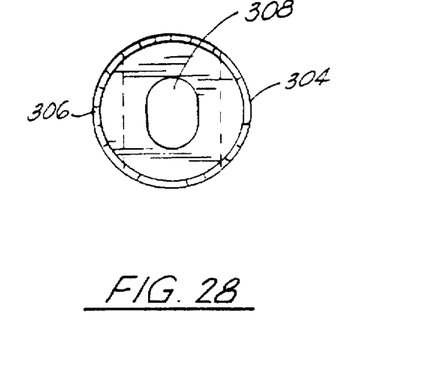
FIG. 28 is a top plan view of the guide member of FIG. 26.
Figure 29:
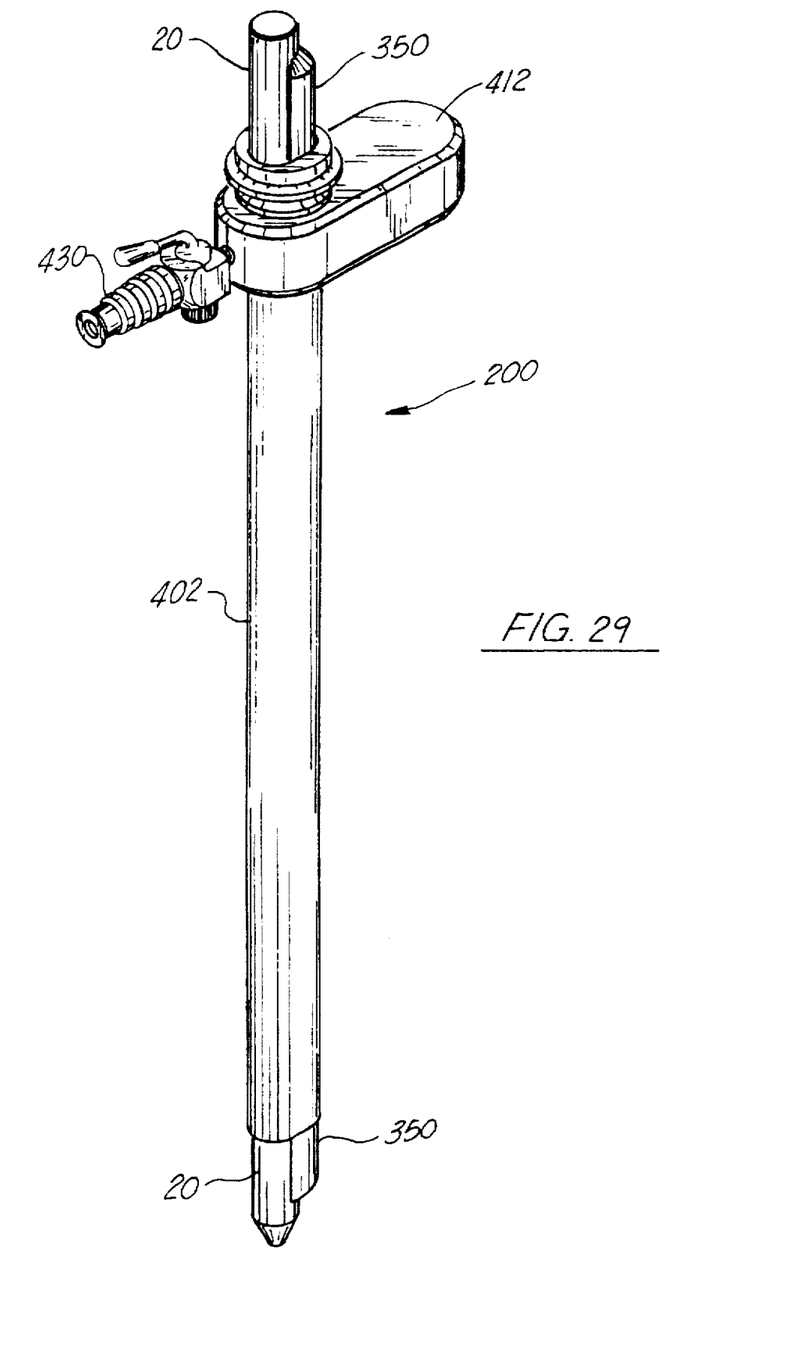
FIG. 29 is a perspective view of an assembly of the alternate embodiment of the subject invention.

An alternate embodiment of the oval cannula 110 is an oval cannula assembly 200 (FIG. 29) The oval cannula assembly 200 includes the cannulated obturator 20, a guide 300, an elongated member 350, and an oval cannula apparatus 400. Guide 300 is formed from a solid cylinder 302 having opposing sides 304, 306 and a centrally located through bore 308 (FIGS. 26–28). Bore 308 is generally ovoid in shape and is shaped to allow the cannulated obturator 20 and an elongated member 350 to nest in relation to each other when the cannulated obturator 20 and elongated member 350 are inserted through guide 300. Opposing sides 304, 306 of the cylinder 302 can include indentations 310 that enable a surgeon's fingers to firmly grip the guide 300 during the surgical procedure. Cylinder 302 has an outer surface 311 that can include serrations 312 over a portion of the outer surface 311 (FIG. 27). The indentations 310 have an outer surface 314 that is smooth. In a preferred embodiment, the indentations 310 are generally circular and concave in shape.

The elongated member 350 has a cross-sectional shape such that when placed adjacent to the cannulated obturator 20, the elongated member 350 and the obturator 20 form an assembly having an oval cross-section.

Figure 24:
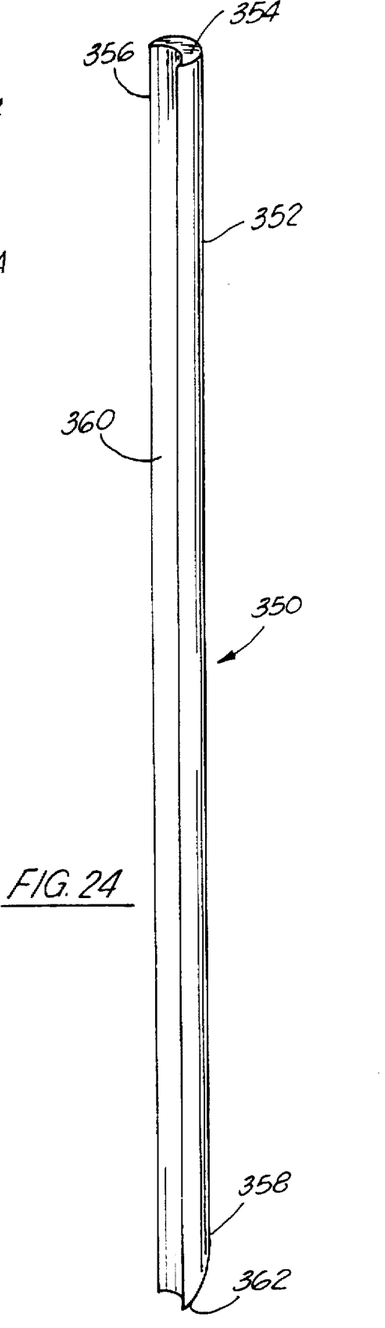
FIG. 24 side plan view of an alternate embodiment of the subject invention illustrating a half-moon rail.

An example of such a cross-sectional shape is a half moon rail that includes an elongated grooved member 352 having a generally crescent-shaped cross section 354 (FIG. 24). Other elongated members with different cross-sectional shapes could be used to form the oval cross-sectional assembly. Elongated member 352 has a proximal end portion 356 and a distal end portion 358. The proximal end portion 356 has a generally flat surface.

The distal end portion 358 includes a taper 362 to allow insertion of the elongated member 352 into the back of the patient and into the percutaneously created fenestration of the annulus of the disc. Elongated member 352 includes a longitudinal groove 360 that is sized and shaped to cradle the cannulated obturator 20. Longitudinal groove 360 of the elongated member 350 allows the cannulated obturator 20 and elongated member 350 to be nested together and form a generally oval shape which fits through the oval bore 308 of guide 300.

Figure 23:
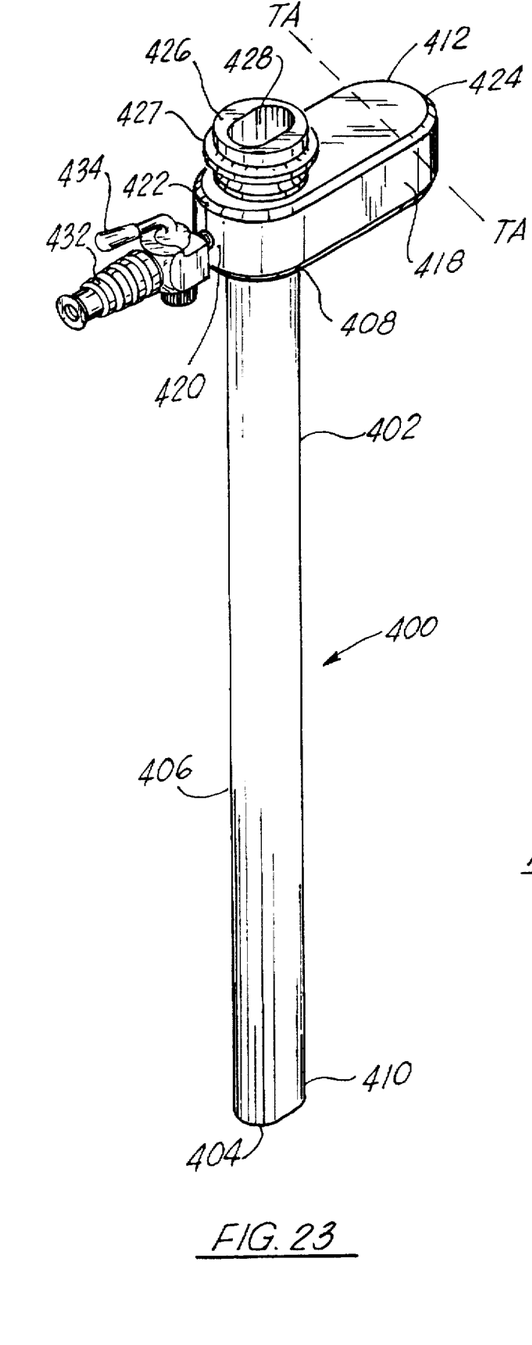
FIG. 23 is a perspective view of an alternate embodiment of the subject invention illustrating an oval cannula apparatus.

Oval cannula apparatus 400, as illustrated in FIGS. 23 and 25, includes an elongated tube 402 with an inner bore 404 having a transverse cross section that is defined by an X axis D1 and a Y axis D2 that forms a generally ovoid shape (FIG. 25A). The X axis D1 has a dimension generally between about 5 to 22 millimeters and the Y axis D2 has a dimension generally between about 3 to 11 millimeters. The elongated tube 402 has a longitudinal length of generally between about 50 to 250 millimeters. Elongated tube 402 has an outer surface 406, a proximal end 408 and a distal end 410.

A collar portion 412 is attached to elongated tube 402 at its proximal end 408. Collar portion 412 has a longitudinal axis LA (FIG. 25), a transverse axis TA (FIG. 23), an upper surface 414, and a lower surface 416. In a preferred embodiment, collar portion 412 has a generally rectangular shape with longitudinal opposing side walls 418 positioned between the upper and lower surfaces 414, 416 along the longitudinal axis LA and transverse opposing side walls 420 positioned between the upper and lower surfaces 414, 416 along the transverse axis TA. Preferably, collar portion 412 is formed from a solid piece of material with a rounded first end 422 and rounded a second end 424. The elongated tube 402 extends through the collar portion 412 from its lower surface 416 to its upper surface. In a preferred embodiment, elongated tube 402 extends through collar portion 412 generally proximal to the first end 422 of collar portion 412. The elongated tube 402 creates a continuous channel 417 from the upper surface 414 to the lower surface 416 of collar portion 412 through the distal end 410 of elongated tube 402. An elevated cylindrical member 426 extends from the upper surface 414 of collar portion 412 in alignment with the elongated tube 402. Cylindrical member 426 forms a first opening 428 with the continuous channel 417 of elongated member 402 that extends through the distal end 410 of elongated tube 402. Cylindrical member 426 has a an outer surface 427 that includes one or more annular grooves 429 (FIG. 25).

Collar portion 412 includes a second opening 430 that communicates with the continuous channel 417 of elongated tube 402. The second opening 430 is preferably placed through the transverse opposing side wall 420 at the first end 422 of collar portion 412 perpendicular to and communicating with the continuous channel 417 of elongated tube 402. A valve 432 is connected to the second opening 430 of collar portion 412, with valve 432 extending outwardly from the transverse opposing side wall 420 at the first end 422 of collar portion 412. Valve 432 can be opened and closed by the user to allow controlled outflow of a fluid and is of a type known by those skilled in the art. In preferred embodiment, valve 432 is a manually operable type valve with a stop cock mechanism 431 for opening and closing the valve 432.

Figure 30:
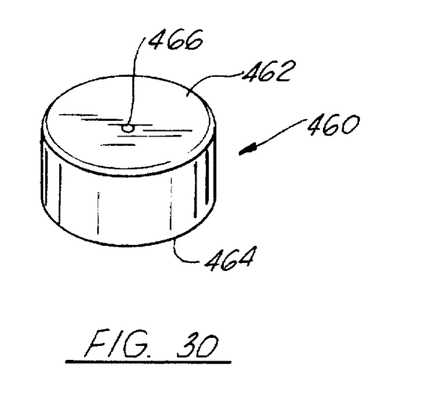
FIG. 30 is a top perspective view of an alternate embodiment of the subject invention illustrating a sealing member.
Figure 31:
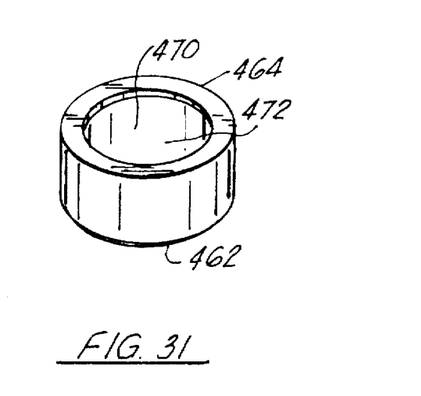
FIG. 31 is a bottom perspective view of the sealing member of FIG. 30.
Figure 32:
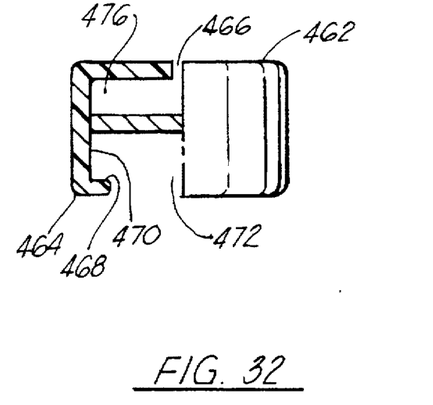
FIG. 32 is a side plan view in partial cross section of the sealing member of FIG. 30.
Figure 33:
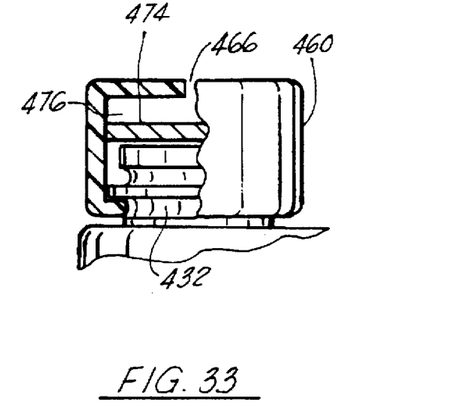
FIG. 33 is a side plan view in partial cross section of the sealing member of FIG. 30 in place on the oval cannula apparatus of FIG. 23.

Oval cannula assembly 200 can also include a sealing means or cap 460 for sealing the first opening 428 of the oval cannula apparatus 400 for use with an irrigation system (not shown). The sealing cap 460 prevents the outflow of fluids through the first opening 428 when an irrigation device is inserted through the cap 460. Cap 460 is generally cylindrical in shape and is formed of a pliable material such as silicon rubber which allows an irrigation device to be inserted through a small opening in cap 460 but prevents the outflow of fluid through the cap 460. Sealing cap 460 has a top portion 462 and a bottom portion 464, with top portion 462 having a centrally located opening 466 for the insertion of the irrigation device.

Bottom portion 464 of cap 460 includes a lip 468 that is sized and shaped to engage the annular grooves 429 of the cylindrical member 426 in order to securely fasten cap 460 to the cylindrical member 462 of the oval cannula apparatus 400. Cap 460 contains interior walls 470 that form an interior opening 472 in cap 460. The interior opening 472 includes a barrier wall 474 placed horizontally to and spaced apart from the top portion 462 of cap 460. Barrier wall 474 is connected to and is part of the interior walls 470 of cap 460 and creates an upper chamber 476 within the interior opening 472 of cap 460. The barrier wall 474 prevents the outflow of fluid through the first opening 428 when the irrigation device is placed through opening 466 in the top portion 462 of the cap 460. In a preferred embodiment, barrier wall 474 can contain a small horizontal cut for ease in inserting the irrigation device through the cap 460. When a closed irrigation system is desired, the irrigation device is inserted through opening 466 and barrier wall 474 of cap 460 and is placed into the continuous channel 417 of elongated tube 402. A suction device, known to one skilled in the art, is connected to valve 432 for suctioning fluid out of the second opening 428 and through valve 432. Thus, when cap 460 is attached to the cylindrical member 426, the oval cannula apparatus 400 allows for a closed irrigation system wherein the fluid is introduced into the first opening 428 and circulates through the continuous channel 417, out the distal end 410 of elongated tube 402 and into the operating site and up and out the second opening 430 and the valve 432 by means of the suction device connected to valve 432. When the irrigation system is not required, the sealing cap 460 is removed from the cylindrical member 426 and the surgical instruments and viewing device are inserted through the first opening 428 and down the elongated tube 402 in order to perform the surgical disc procedure.

The guide 300, the elongated member 350 and the oval cannula apparatus 400 are preferably formed from a bio-compatible material such as stainless steel or austinitic stainless steel.

Figure 34:
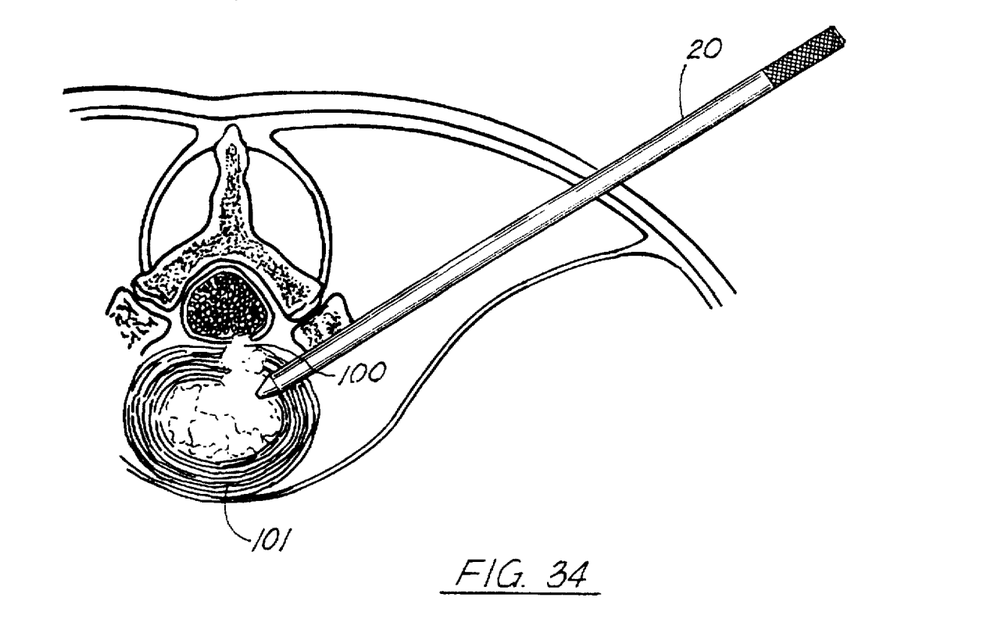
FIG. 34 is a schematic view of the cannulated obturator of FIG. 2 inserted into a herniated disc.

When the oval cannula 110 or the oval cannula assembly 200 is used in a percutaneous surgical disc procedure, uniportal access to the intervertebral disc space is established by advancing a guidewire 10 through the skin of a patient's back posterolaterally under flouroscopic observation until the guidewire 10 contacts the exterior symptomatic side of the annulus fibrosis of the herniated disc. The cannulated obturator 20 is passed over the guidewire 10 until the distal end of the cannulated obturator 20 contacts the external surface of the annulus fibrosis of the herniated disc (FIG. 34). Thereafter, a cannulated obturator 20 (FIG. 2), having a lumen with a diameter slightly larger than that of the guidewire 10, is passed over the guidewire 10 until the cannulated obturator 20 contacts the external surface of the annulus fibrosis of the herniated disc. The removal of the guidewire 10 at this point is optional. An access cannula 30a (FIG. 3), suitably of about 0.25 in. outer diameter and having external gradations 31 of 10 mm, is then passed over the cannulated obturator 20 and advanced to the external surface of the annulus fibrosis. At this point, the guidewire 10 is removed if not previously removed. The inner diameter of the access cannula 30a is sized to closely fit over the cannulated obturator 20. The cannulated obturator 20 is then removed, and a 3 mm or 5 mm trephine 40 (FIG. 4) is introduced through the access cannula 30a. The trephine 40 has a plurality of saw teeth 40a or other cutting members. The trephine 40 is advanced into the annulus of the disc, with rotation, creating an annular fenestration (that is, a bore) through the annulus fibrosis into the nucleus. The trephine 40 is then removed.

Figure 35:
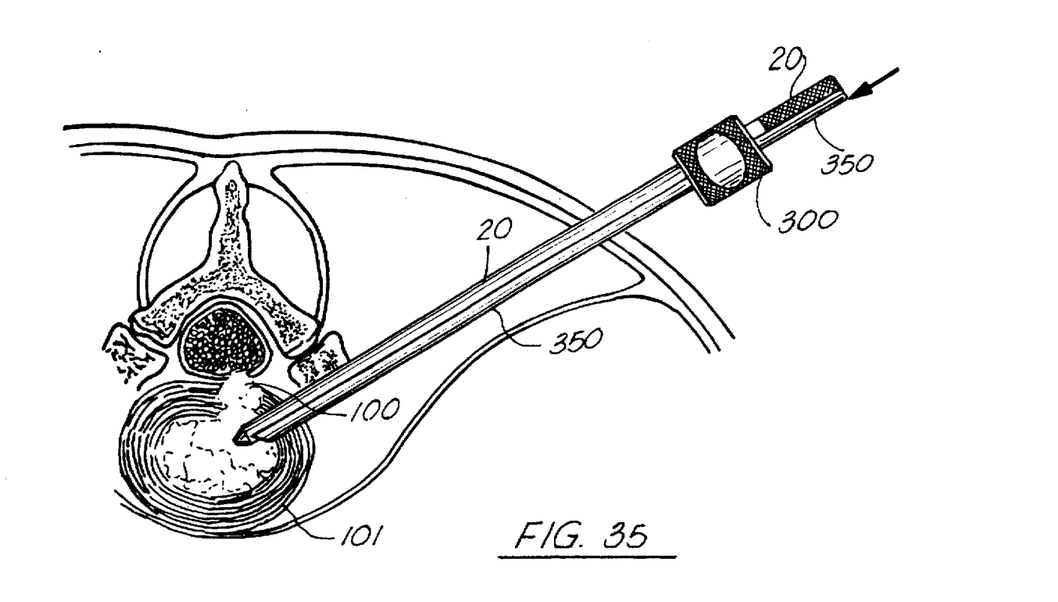
FIG. 35 is a schematic view of the cannulated obturator of FIG. 2 and the rail of FIG. 24 inserted into the disc illustrating the use of the guide member of FIG. 26.

The cannulated obturator 20 is reintroduced into the access cannula 30a and passed into the fenestration of the annulus. Fluoroscopic guidance may be utilized. The access cannula 30a is then removed. Guide 300 is placed over the cannulated obturator 20 with the oval bore 308 of guide 300 allowing for the insertion of the elongated member 350 through guide 300 and placing the elongated member 350 in nesting relationship with the cannulated obturator 20 (FIG. 35). The nested cannulate obturator 20 and elongated member 350 fill the opening of the oval bore 308 of guide 300 and create an assembly that has a generally oval cross-section. The tapered end 362 of the elongated member 350 allows it to be easily inserted into the back of the patient and to be easily wedged into the disc, along the side of the obturator 20.

Figure 36:
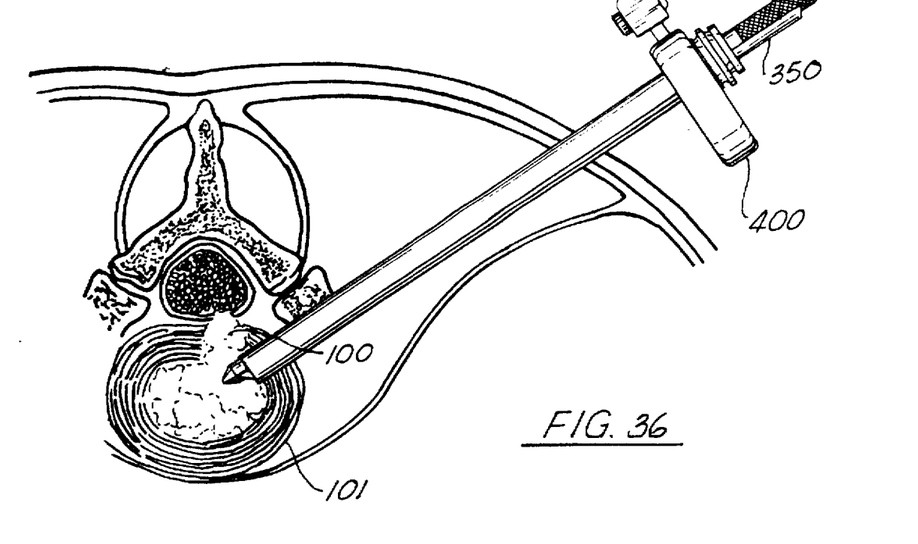
FIG. 36 is a schematic view of an assembly of the oval cannula apparatus of FIG. 23, the cannulated obturator of FIG. 2 and the rail of FIG. 24 inserted into the disc.
Figure 37:
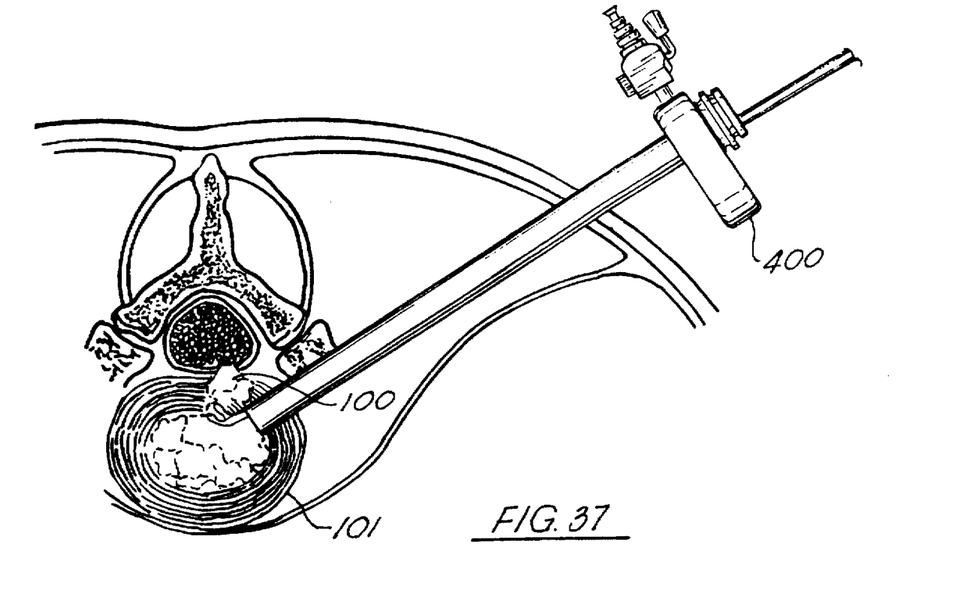
FIG. 37 is a schematic view of a surgical procedure being performed through the oval cannula apparatus of FIG. 23 inserted into the herniated disc.

The guide 300 is removed from the nested cannulated obturator 20 and elongated member 350 and the oval cannula 110 or oval cannula apparatus 400 is slid downwardly over the nested cannulated obturator 20 and the elongated member 350 (FIG. 36) with the distal end 410 of the oval cannula apparatus 400 or the oval canula 110 being inserted into the annulus of the disc. The cannulate obturator 20 and elongated member 350 are removed from the oval cannula 110 or oval cannula apparatus 400 and the disc and the surgical procedure is preformed by introducing both the surgical instruments and/or the viewing apparatus into the oval cannula 110 or oval cannula apparatus 400 (FIG. 37). If a closed irrigation system is desired, the sealing cap 460 can be placed over the cylindrical member 426 is with the irrigation device being placed through the cap 460. A suction device is applied to valve 432 which will provide for a continuous flow of fluid from the first opening 426, through the elongated tube 402 and out the second opening 430 and valve 432.

It should be understood that there can be improvements and modifications made to the embodiments of the invention described in detail above without departing from the spirit or scope of the invention, as set forth in the accompanying claims.

What is claimed is:

1. A percutaneous surgical disc procedure, comprising the steps of:
   a) percutaneously entering the back of a patient in a posterolateral position with an obturator having a lumen;
   b) advancing the obturator through a percutaneously created fenestration of the annulus of the disc;
   c) placing a guide containing a generally oval shaped bore over the obturator;
   d) inserting an elongated member through the bore of the guide and into the back of the patient into the percutaneously created fenestration of the annulus of the disc, the elongated member having a cross-sectional shape such that when placed adjacent to the obturator, forms an assembly having an oval cross-section;
   e) removing the guide from the obturator and elongated member assembly;
   f) sliding an oval cannula having a bore with an oval transverse cross-section and proximal and distal ends, downwardly over the obturator and elongated member assembly;
   g) inserting the distal end of the oval cannula into the disc;
   h) removing the obturator and elongated member assembly from the bore of the oval cannula and the disc; and
   i) introducing multiple surgical instruments into the oval cannula to perform the surgical procedure.

2. The percutaneous surgical disc procedure of claim 1, wherein the multiple surgical instruments include a viewing means for viewing the surgical procedure.

3. The percutaneous surgical disc procedure of claim 1, wherein the oval cannula includes an elongated tube and means for introducing a continuous fluid flow through the elongated tube for providing an irrigation system for the percutaneous surgical disc procedure.

4. The percutaneous surgical disc procedure of claim 3, wherein the means for introducing a continuous fluid flow includes first and second openings that allow for the introduction of a fluid through the first opening and the continuous flow of fluid through the elongated tube and out the second opening.

5. The percutaneous surgical disc procedure of claim 4, wherein the first opening is formed to accept a sealing means that enables fluid inflow while preventing the outflow of the fluid.

6. The percutaneous surgical disc procedure of claim 4, wherein the second opening includes a value that can be opened and closed by the user for controlling outflow of the fluid.

7. The percutaneous surgical disc procedure of claim 1, wherein the guide is in the form of a solid cylinder having opposing sides and a centrally located through bore, the bore being generally ovoid in shape for allowing the obturator and elongated member assembly to nest in relation to each other when the obturator and elongated member are inserted through the guide.

8. The percutaneous surgical disc procedure of claim 7, wherein the opposing sides of the solid cylinder including indentations that enable a surgeon's fingers to firmly grip the guide.

9. The percutaneous surgical disc procedure of claim 7, wherein the solid cylinder has an outer surface that includes serrations over a portion of the outer surface.

10. The percutaneous surgical disc procedure of claim 1, wherein the elongated member has a generally crescent-shaped cross-section and proximal and distal end portions and a longitudinal groove that is sized and shaped to cradle the obturator.

11. The percutaneous surgical disc procedure of claim 10, wherein the distal end of the elongated member is tapered to allow insertion of the elongated member into the back of the patient and into the percutaneously created fenestration of the annulus of the disc.

12. An apparatus for use in a percutaneous surgical disc procedure wherein the disc has an annulus, comprising:
   a) an oval cannula having an elongated tube with an inner bore, an outer surface, and a transverse cross section that is defined by an X axis and a Y axis, wherein the X axis dimension is greater that the Y axis dimension so that the bore has a generally ovoid shape, the elongated tube having proximal and distal ends;
   b) the inner bore being sized and shaped to allow an obturator and an elongated member to fit inside the inner bore when the obturator and elongated member are adjacent to one another and form an assembly with an oval cross-section;
   c) the oval shaped bore of the oval cannula enabling a user to insert more than one instrument at a time into the bore when the obturator and elongated member have been removed from the oval shaped bore.
   further comprising a collar portion with a longitudinal axis, a transverse axis, and upper and lower surfaces, longitudinal opposing side walls positioned between the upper and lower surfaces along the longitudinal axis, and transverse opposing side walls positioned between the upper and lower surfaces along the transverse axis, the collar portion having first and second end with the elongated tube extending through the collar portion from the lower surface to the upper surface proximal to the first end of the collar portion, further comprising an elevated cylinder extending from the upper surface of the collar portion in alignment with the elongated tube forming a first opening and a continuous channel from the opening of the elevated cylinder through the distal end of the elongated tube.

13. An apparatus for use in a percutaneous surgical disc procedure wherein the disc has an annulus, comprising:
   an oval cannula having an elongated tube with an inner bore, an outer surface, and a transverse cross section that is defined by an X axis and a Y axis, wherein the X axis dimension is greater that the Y axis dimension so that the bore has a generally ovoid shape, the elongated tube having proximal and distal ends;
   b) the inner bore being sized and shaped to allow an obturator and an elongated member to fit inside the inner bore when the obturator and elongated member are adjacent to one another and form an assembly with an oval cross-section;

c) the oval shaped bore of the oval cannula enabling a user to insert more than one instrument at a time into the bore when the obturator and elongated member have been removed from the oval shaped bore, further comprising a collar portion with a longitudinal axis, a transverse axis, and upper and lower surfaces, longitudinal opposing side walls positioned between the upper and lower surfaces along the longitudinal axis, and transverse opposing side walls positioned between the upper and lower surfaces along the transverse axis, the collar portion having first and second end with the elongated tube extending through the collar portion from the lower surface to the upper surface proximal to the first end of the collar portion, further comprising a valve extending outwardly from the transverse opposing side wall at the first end of the collar portion, the valve forming a second opening communicating with the continuous channel of the elongated tube.

14. An apparatus for use in a percutaneous surgical disc procedure wherein the disc has an annulus, comprising:

a) an oval cannula having an elongated tube with an inner bore, an outer surface, and a transverse cross section that is defined by an X axis and a Y axis, wherein the X axis dimension is greater that the Y axis dimension so that the bore has a generally ovoid shape, the elongated tube having proximal and distal ends;

b) a collar portion with a longitudinal axis, a transverse axis, and upper and lower surfaces, longitudinal opposing side walls positioned between the upper and lower surfaces along the longitudinal axis, and transverse opposing side walls positioned between the upper and lower surfaces along the transverse axis, the collar portion having first and second ends;

d) the elongated tube extending through the collar portion from the lower surface to the upper surface proximal to the first end of the collar portion;

e) an elevated cylinder extending from the upper surface of the collar portion in alignment with the elongated tube forming a first opening and a continuous channel from the opening of the elevated cylinder through the distal end of the elongated tube; and f) a valve extending outwardly from the transverse opposing side wall at the first end of the collar portion, the valve forming a second opening communicating with the continuous channel of the elongated tube.

15. The apparatus of claim 14, wherein the elevated cylinder has an outer surface that includes at least one annular groove.

16. The apparatus of claim 15, wherein the outer surface of the elevated cylinder includes a plurality of grooves.

17. The apparatus of claim 14, wherein the valve can be opened and closed by the user to allow controlled outflow of a fluid.

18. The apparatus of claim 17, wherein the valve is manually operable.

19. The apparatus of claim 14, wherein the oval cannula apparatus includes a sealing means for sealing the first opening in order to prevent the outflow of fluid through the first opening, the sealing means being formed to allow a fluid inflow device to be inserted through the sealing means while preventing the outflow of fluid through the sealing means.

20. The apparatus of claim 14, wherein the elongated tube and the first and second openings of the oval cannula allow for the introduction of a fluid through the first opening and the continuous flow of fluid through the elongated tube and out the second opening, providing an irrigation system for the percutaneous surgical disc procedure.

21. The apparatus of claim 14, wherein the elongated tube generally has a Y axis dimension of between about 3 to 11 millimeters and an X axis dimension of between about 5 to 22 millimeters and a length of between about 50 to 250 millimeters.

22. An apparatus for percutaneously performing surgical procedures on the spinal region of a patient, comprising:

a) a obturator for advancing through a percutaneously created fenestration of the annulus of the disc of a patient;

b) an elongated member;

c) the combination of the elongated member and the obturator having a generally oval shape upon assembly when the obturator is placed adjacent to elongated member;

d) a guide for guiding the obturator and elongated member together in an adjacent position;

e) an oval cannula having a generally oval shaped bore that can removably receive the obturator and elongated member assembly, the oval shaped bore enabling a user to insert more than one instrument at a time into the bore when the obturator and the elongated member have been removed from the oval shaped bore.

23. The apparatus of claim 22, further comprising means for withdrawing fluid from the oval shaped bore.

24. The apparatus of claim 23, further comprising valve means for controlling the flow of fluid from the oval shaped bore.

25. The apparatus of claim 22, wherein the oval cannula further comprises an enlarged fitting at a proximal end of the oval cannula.

26. The apparatus of claim 25, wherein the enlarged fitting is sized and shaped to engage a sealing member, the sealing member being formed to allow a fluid inflow device to be inserted through the sealing member while preventing the outflow of fluid through the sealing member.

27. The apparatus of claim 22, wherein the guide allows for guiding and holding the obturator and elongated member together independently of the oval cannula.

28. The apparatus of claim 27, wherein the guide means comprises a body with an outer surface and a bore that closely conforms to the assembled obturator and elongated member.

29. An apparatus for percutaneously performing surgical procedures on the spinal region of a patient, comprising:

a) means, including an obturator having a lumen and an outer surface, for forming a fenestration formed in a patient's back and spinal disc and advancing said apparatus into said fenestration;

b) an elongated member having a longitudinal groove that is sized and shaped to receive a portion of the outer surface of the obturator, the groove being so shaped in transverse cross-section that a longitudinally extending portion of the obturator can occupy and nest in the groove;

c) the combination of the elongated member and the obturator having a generally oval shape upon assembly when the obturator closely fits into the groove; and d) an oval cannula that has a generally oval shaped bore that can removably receive the combination of the elongated member and the obturator, the oval shaped bore enabling a user to insert surgical instruments into the bore during disc surgery.

* * * * *